United States Patent [19]

Wojtowski

[11] Patent Number: 5,228,853
[45] Date of Patent: Jul. 20, 1993

[54] METHOD FOR DETERMINING A SENSITIVE TOOTH

[75] Inventor: Paul W. Wojtowski, Wilmington, Del.

[73] Assignee: E. I. Du Pont de Nemours and Company, Wilmington, Del.

[21] Appl. No.: 734,361

[22] Filed: Jul. 17, 1991

[51] Int. Cl.⁵ .............................................. A61C 5/00
[52] U.S. Cl. ................................... 433/215; 433/141
[58] Field of Search ........................................ 433/215

[56] References Cited

U.S. PATENT DOCUMENTS 3,734,081  5/1973  Schaack ............................... 433/215
4,828,494  5/1989  Angus et al. ......................... 433/215

FOREIGN PATENT DOCUMENTS 0034278  5/1973  Japan .................................... 433/215

OTHER PUBLICATIONS

"Essentials of Clinical Dental Assisting", Chasteen, 1980, pp. 242-243.
Tooth Slooth ®, "The Professional Image", ad, Long Beach, Calif.

Primary Examiner—John J. Wilson

[57] ABSTRACT

A method for determining which one of a group of teeth is causing pain to a patient upon such group of teeth being exposed to a material wherein a portion of such pain causing material is applied to such teeth one at a time until it is ascertained which tooth is causing the pain. The pain causing material can be mounted on a tape for application to the teeth. Also disclosed is an applicator comprising a hemispherically shaped head, having a cavity, adapted to receive the pain causing material, located in the rounded side of the head opposite the flat side of the hemisphere. The hemispherically shaped head is equipped with a handle for convenient use.

2 Claims, 1 Drawing Sheet

METHOD FOR DETERMINING A SENSITIVE TOOTH

FIELD OF THE INVENTION

The present invention relates to a method for determining exactly which tooth is causing discomfort to a patient due to the sensitivity of such tooth to one or more materials. The method involves applying an appropriate sized portion of such material to a series of teeth, one at a time, until it is ascertained just which tooth is suffering the difficulty. Also within the invention are certain means for applying the material to the individual teeth involved.

BACKGROUND OF THE INVENTION

A diseased or damaged tooth may be sensitive to some material or chemical, a common one being sugar. Patients and dentists can have particular difficulty determining exactly which tooth is or was hurting since that part of the mouth, unlike the lips, does not have separate nerve spacings to discriminate between closely spaced points, and small cracks and holes in a tooth or filling may be difficult or impossible to find by visual or X-ray inspection.

A similar problem may exist with a tooth sensitive to pressure rather than, or in addition to, a material. Solutions to finding the pressure sensitive tooth have been solved, at least in part, by devices which enable applying pressure to only one tooth at a time. U.S. Pat. No. 4,828,494, assigned to Dental Design Systems, Inc., has a ball at one end of a plastic handle. The ball has indentations on opposite sides to receive the ends of cusps of opposing teeth of a patient, who can apply pressure by biting down. Another device on the market is the Tooth Slooth ® which has a small tetrahedron at the head with an indented apex. Neither of these devices provide nor suggest means for testing sensitivity to a material or chemical, for example, sugar.

An object of the subject invention is to provide a simple, rapid and inexpensive means and method for identifying a diseased or damaged tooth with a crack, loose or damaged filling, or other defect allowing an opening to the sensitive inner portion of the tooth, and sensitive to a material or chemical such as sugar or other sweet, salt, acidic, or other offending material or chemical, as well as, perhaps, sensitive to pressure. Other objects will be apparent from the descriptions of the invention.

SUMMARY OF THE INVENTION

An applicator containing a small quantity of a test material is positioned on the tooth to be tested so that the crown and/or side(s) of the tooth to be tested is/are contacted by the material. The patient may bite down on the applicator in order to help force the material into a defect in the tooth or filling. The applicator can be a handle like a toothbrush handle with a small sponge, cup or cavity at the end or it can be a cap to fit over the tooth or simply a strip of material such as cellophane film with a bit of paste or gel containing the test material. The test material can contain sugar (for example, sucrose, glucose, fructose), acid (for example, vinegar, cream of tartar), salt, spice, a particular kind of food which has caused the patient to seek a dentist, or combinations of them. The device may also provide a means for separately or simultaneously testing for pressure sensitivity.

DETAILED DESCRIPTION OF THE DRAWINGS

Figure 1:
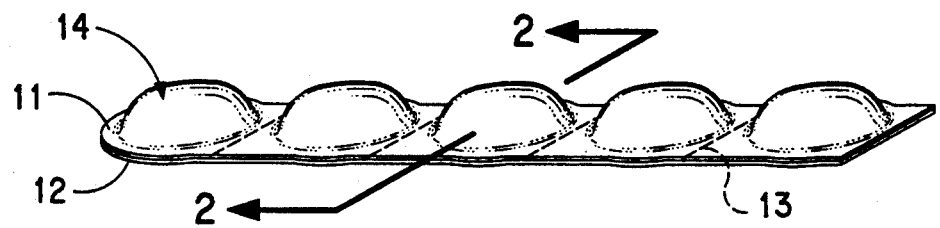
FIG. 1 is a perspective view of a double sheet of film type of applicator used in the present invention.

Referring now to FIG. 1, a pair of superposed films 11 and 12 are depicted which are provided with a plurality of score marks 13 so that individual strips of superposed films can be removed as desired for use. Each of the strips when removed from the main assembly are provided with a portion of test material 14 suitable for being applied to an individual tooth. After being removed from the main assembly the strip 11 is separated from strip 12 while a portion of test material 14 remains with one of strips 11 or 12. This can be facilitated by application of a release agent to the inner surface of one of the strips 11, 12 forming the assembly.

Figure 3:
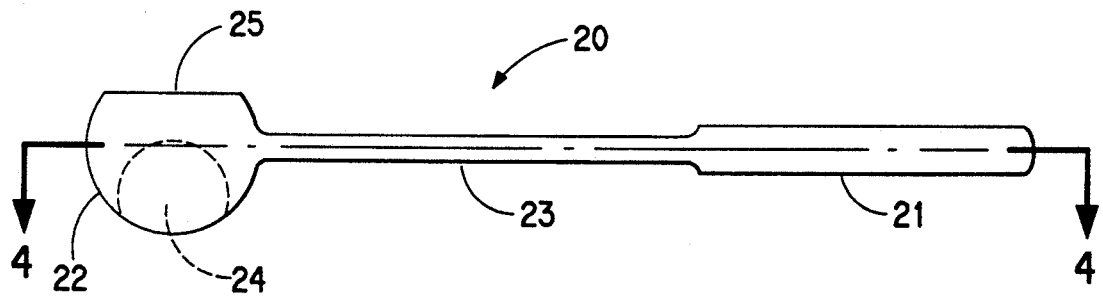
FIG. 3 is a side view of an applicator for use in the present invention.
Figure 4:
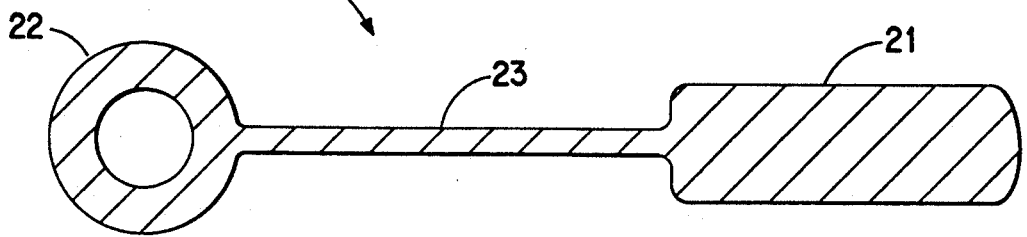
FIG. 4 is a cross-section taken on line 4—4 of FIG. 3.

Referring now to FIG. 3, a mechanical applicator indicated generally at 20 is depicted. Mechanical applicator 20 comprises three portions, handle 21, applicator head 22 and arm 23 connecting handle 21 with applicator head 22. Referring now to FIG. 4, applicator head 22 is provided with a cavity 24 adapted to receive a portion of test material (not shown) and apply it to an individual tooth cusp of a patient. A spongy material 25 covers head 22 and is impregnated with test material.

DETAILED DESCRIPTION OF THE INVENTION

Various alternatives are obvious design choices such as a plastic handle of only moderate hardness so as to allow flexion, an angled handle easier to place in the mouth, a sponge or other porous or fibrous material to hold a liquid, gel, thin fluid or paste, or a cup or cavity, a flexible strip such as plastic film to at least partially wrap around or over the tooth, or even a tube or channel in a handle with means to extrude a bit of liquid, paste or gel onto the tooth with perhaps some pressure. Such pressure will be necessary in some cases to get a prompt pain response, but from experience not needed in most cases for prompt (a second or so, up to about 2 minutes at most) response of pain.

Figure 2:
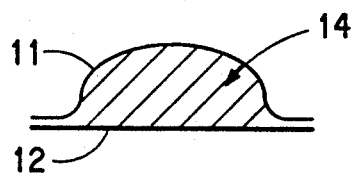
FIG. 2 is a cross-section taken on line 2—2 of FIG. 1.

Another form of a test device is a double sheet of plastic film as depicted in FIGS. 1 and 2 such as polyethylene, polyethylene terephthalate or cellophane, scored to form easily torn strips and segments of strips, with small ($\frac{1}{8}$ to $\frac{1}{4}$ inch diameter by 1/16 inch thick) bits of soft sugar paste, such as soft milk chocolate, in the center of each segment. The film on one side of each test sample is also scored to break readily to release some of the sugar material on the desired tooth surface.

The preferred embodiment of the device of the invention as depicted in FIGS. 3 and 4 has a head size (diameter) slightly less than the diameter of an individual molar. The head is shaped approximately hemispherical with an indentation at the top of the hemisphere opposite the flat side of the handle. The indentation can be placed on the concave surface of the tooth crown or on a tooth cusp. The flat portion can be bitten by the opposing tooth to apply pressure to force the material into a crack or leaky filling. In the case where the test material is a liquid or soft pasty solid, the head is covered with sponge, gauze, fiber mass, or other soft, porous material, which is impregnated with the test material. This can be kept moist or activated by wetting, e.g., water, saliva, etc. The spongy material would not only contain and release the material, but would also reduce the risk of damage to the tooth during biting. The spongy material can also provide better contact of the test material with the tooth surface, i.e., greater overall surface area contact and therefore more thorough application of the test material.

The arm of the device should be sufficiently rigid to maintain the shape of the device to control positioning, but flexible enough to readily bend. It can be approximately the length of a typical pressure testing device or longer. The handle of the device should be flat and large enough to be easily grasped by the fingertips. The device could also be double headed. Thus several head shapes could be possible with heads performing separate functions, e.g., test material application at one end and pressure application using the other end. A handle could be located in the middle or otherwise. A single head is preferred.

The device can also be uniform in shape, i.e., be a strip of film plastic slightly less than the width of a tooth and covered with a spongy material impregnated with the test material as described above. This could be used by cutting or tearing off a suitable length of the strip and using as above.

EXAMPLES

Example 1

A patient claimed to be experiencing tooth pain in the lower rear of the mouth, probably in a molar, while eating, and especially while eating sweets. The patient could not tell exactly in which tooth the pain originated. Due to the presence of multiple fillings in all the molars located in the general area where the pain occurred, it was not possible to unambiguously identify the offending tooth by simple visual inspection. A small, pea-sized piece of soft milk chocolate was adhered to one side of a piece of cellophane tape approximately one-half inch (1.27 cm) wide by approximately 2-3 inches (5.08-7.62 cm) long. The chocolate on the tape was placed on the biting surface of one individual suspected molar, and then bitten by the patient. The tape was then moved sequentially to adjacent individual molars and the chocolate bitten each time. The offending tooth was located upon biting by the immediate sensation of pain by the patient in only one of the tested teeth and not in the others. Upon repetition of the procedure, the same result occurred verifying the original diagnosis. Upon this unambiguous identification of the offending tooth, treatment could begin.

I claim:

1. A process for ascertaining which one of a group of teeth is causing pain when exposed to a chemical selected from the group consisting of sugar and acid, the process comprising applying a portion of said chemical to each member of said group of teeth individually in turn until it is determined which individual tooth is causing the pain.

2. The process of claim 1 wherein a portion of the chemical being applied is mounted on a strip tape.

* * * * *

UNITED STATES PATENT AND TRADEMARK OFFICE
CERTIFICATE OF CORRECTION

PATENT NO. : 5,228,853

DATED : July 20, 1993

INVENTOR(S) : Paul W. Wojtkowski

It is certified that error appears in the above-identified patent and that said Letters Patent is hereby corrected as shown below:

On title page, item [19], "Wojtowski" should read --Wojtkowski--
               item [75], "Wojtowski" should read --Wojtkowski--

Signed and Sealed this

Twelfth Day of April, 1994

Attest:

BRUCE LEHMAN

*Commissioner of Patents and Trademarks*

*Attesting Officer*